United States Patent
Liu et al.

(10) Patent No.: US 9,488,737 B2
(45) Date of Patent: Nov. 8, 2016

(54) SYSTEM AND METHOD FOR IMAGE COMPRESSION IN X-RAY IMAGING SYSTEMS

(71) Applicant: GENERAL ELECTRIC COMPANY, Schenectady, NY (US)

(72) Inventors: James Zhengshe Liu, Salt Lake City, UT (US); Richard Larry Anderton, West Jordan, UT (US); Brian James Grekowicz, Salt Lake City, UT (US); Bela Janos Kiraly, Salt Lake City, UT (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 13 days.

(21) Appl. No.: 14/567,039

(22) Filed: Dec. 11, 2014

(65) Prior Publication Data

US 2015/0092922 A1     Apr. 2, 2015

Related U.S. Application Data

(63) Continuation of application No. 13/588,760, filed on Aug. 17, 2012, now Pat. No. 8,942,444.

(51) Int. Cl.

| | | |
|---|---|---|
| *G06K 9/00* | (2006.01) | |
| *G01T 1/17* | (2006.01) | |
| *H04N 5/32* | (2006.01) | |
| *H04N 5/378* | (2011.01) | |
| *A61B 6/00* | (2006.01) | |

(52) U.S. Cl.
CPC ................. *G01T 1/17* (2013.01); *A61B 6/563* (2013.01); *H04N 5/32* (2013.01); *H04N 5/378* (2013.01)

(58) Field of Classification Search
USPC ........ 382/128, 131, 132, 209, 278; 128/922, 128/923
See application file for complete search history.

(56) References Cited

U.S. PATENT DOCUMENTS

| | | | | |
|---|---|---|---|---|
| 7,031,423 | B2* | 4/2006 | Tsukagoshi | A61B 6/032 378/19 |
| 7,230,708 | B2* | 6/2007 | Lapotko | G01N 21/171 356/432 |
| 7,385,217 | B2* | 6/2008 | Tezuka | H04N 1/21 250/586 |
| 7,496,619 | B2* | 2/2009 | Aldroubi | G06T 5/001 708/446 |
| 7,570,185 | B2* | 8/2009 | Rao | H03M 1/1028 341/118 |
| 7,680,314 | B2* | 3/2010 | Hong | G06T 7/0087 382/131 |
| 7,756,240 | B2* | 7/2010 | Nishide | A61B 6/4035 378/5 |
| 7,787,678 | B2* | 8/2010 | Unal | G06T 7/0012 382/128 |
| 7,865,000 | B2* | 1/2011 | Yokoyama | G06T 7/0012 382/128 |
| 8,077,953 | B2* | 12/2011 | Qu | A61B 6/481 382/130 |
| 8,295,435 | B2* | 10/2012 | Wang | A61N 5/10 378/65 |
| 8,670,040 | B2* | 3/2014 | Nokita | G06T 5/003 348/222.1 |

* cited by examiner

*Primary Examiner* — Yosef Kassa
(74) *Attorney, Agent, or Firm* — Fletcher Yoder, P.C.

(57) ABSTRACT

An imaging system includes an analog-to-digital converter configured to convert an analog pixel value into a first digital pixel value. The imaging system also includes an index value source configured to receive the first digital pixel value from the analog-to-digital converter and to generate a digital index value based on a comparison of the first digital pixel value to a digital reference value. In addition, the imaging system includes a transmitter in communication with the index value source and configured to transmit the digital index value. Further, the imaging system includes an image processing component configured to receive the digital index value and to generate a second digital pixel value based at least in part on the received digital index value and a lookup table of the image processing component.

12 Claims, 7 Drawing Sheets

SYSTEM AND METHOD FOR IMAGE COMPRESSION IN X-RAY IMAGING SYSTEMS

CROSS-REFERENCE TO RELATED APPLICATION

This application claims priority to and the benefit of U.S. patent application Ser. No. 13/588,760, entitled "SYSTEM AND METHOD FOR IMAGE COMPRESSION IN X-RAY IMAGING SYSTEMS", filed Aug. 17, 2012, which is herein incorporated by reference in its entirety.

BACKGROUND

The subject matter disclosed herein relates to X-ray imaging systems and more particularly to image compression over a communication channel in X-ray imaging systems.

Digital X-ray imaging systems are becoming increasingly widespread for producing digital data which can be reconstructed into useful radiographic images. In current digital X-ray imaging systems, radiation from a source is directed toward a subject, typically a patient in a medical diagnostic application. A portion of the radiation passes through the patient and impacts a detector. The surface of the detector converts the radiation to light photons that are sensed. The detector is divided into a matrix of discrete picture elements or pixels, and encodes output signals based upon the quantity or intensity of the radiation impacting each pixel region. The detector communicates the encoded output signals to a host computer, which processes the image received based on the digital pixel values. This communication takes place over a communication channel, which may include a tether or a wireless link, between the detector and the computer. Unfortunately, it often takes a long time to send the digital pixel values over the communication channel because of the size of the digital representation needed to maintain sufficient gray levels of the X-ray image. Accordingly, it is now recognized that there is a need for reducing image transfer time across the communication link, without an undesirable loss of gray levels or increase in noise.

BRIEF DESCRIPTION

In one embodiment of the present disclosure, an imaging system includes an analog-to-digital converter configured to convert an analog pixel value into a first digital pixel value. The imaging system also includes an index value source configured to receive the first digital pixel value from the analog-to-digital converter and to generate a digital index value based on a comparison of the first digital pixel value to a digital reference value. In addition, the imaging system includes a transmitter in communication with the index value source and configured to transmit the digital index value. Further, the imaging system includes an image processing component configured to receive the digital index value and to generate a second digital pixel value based at least in part on the received digital index value and a lookup table of the image processing component.

In another embodiment of the present disclosure, a method of operating an imaging system includes converting an analog pixel value to a first digital pixel value using a linear analog-to-digital converter. The method also includes generating a digital index value based on a comparison of the first digital pixel value to a digital reference value using a digital comparator. Further, the method includes mapping the generated digital index value to a second digital pixel value via an image processing component. The second digital pixel value has a larger bit-width than the digital index value.

In a further embodiment of the present disclosure, a digital X-ray detector for use in an imaging system includes a linear analog-to-digital converter configured to convert an analog pixel value received from a detector element to a digital pixel value. The digital X-ray detector also includes an index value source configured to receive the digital pixel value and to generate a digital index value corresponding to the received digital pixel value. The digital index value has a smaller bit-width than the digital pixel value. The digital X-ray detector is configured to communicate the digital index value to a separate image processing component.

BRIEF DESCRIPTION OF THE DRAWINGS

These and other features, aspects, and advantages of the present subject matter will become better understood when the following detailed description is read with reference to the accompanying drawings in which like characters represent like parts throughout the drawings, wherein.

DETAILED DESCRIPTION

Present embodiments are directed to systems and methods for reducing image transfer time over a communication channel between a digital X-ray detector and an image processing component within an X-ray imaging system. The X-ray detector includes an analog-to-digital converter to change a detected analog signal, which is representative of an image pixel, to a digital representation. The digital representation may be a certain bit-width (e.g., 14-bit) to maintain a desired number of gray levels in the image. Gray levels refer to a gradient of different pixel intensities within an image, between 0% intensity (e.g., black) and 100% intensity (e.g., white). The X-ray detector also includes an index value source that uses a digital comparator and a lookup table to generate an index value for each of the digital pixel values. The index values may have a smaller bit-width than the digital pixel values they are based upon, allowing for reduced transfer time across the communication channel. The lookup table may include a mapping of the digital pixel values to the digital index values, and a similar lookup table may be resident in the image processing component for converting the digital index values back to a pixel representation with a larger bit-width. This mapping may be at least partially quadratic, based on a relationship between X-ray quantum noise in the signal and quantization noise due to the image compression.

Figure 1:
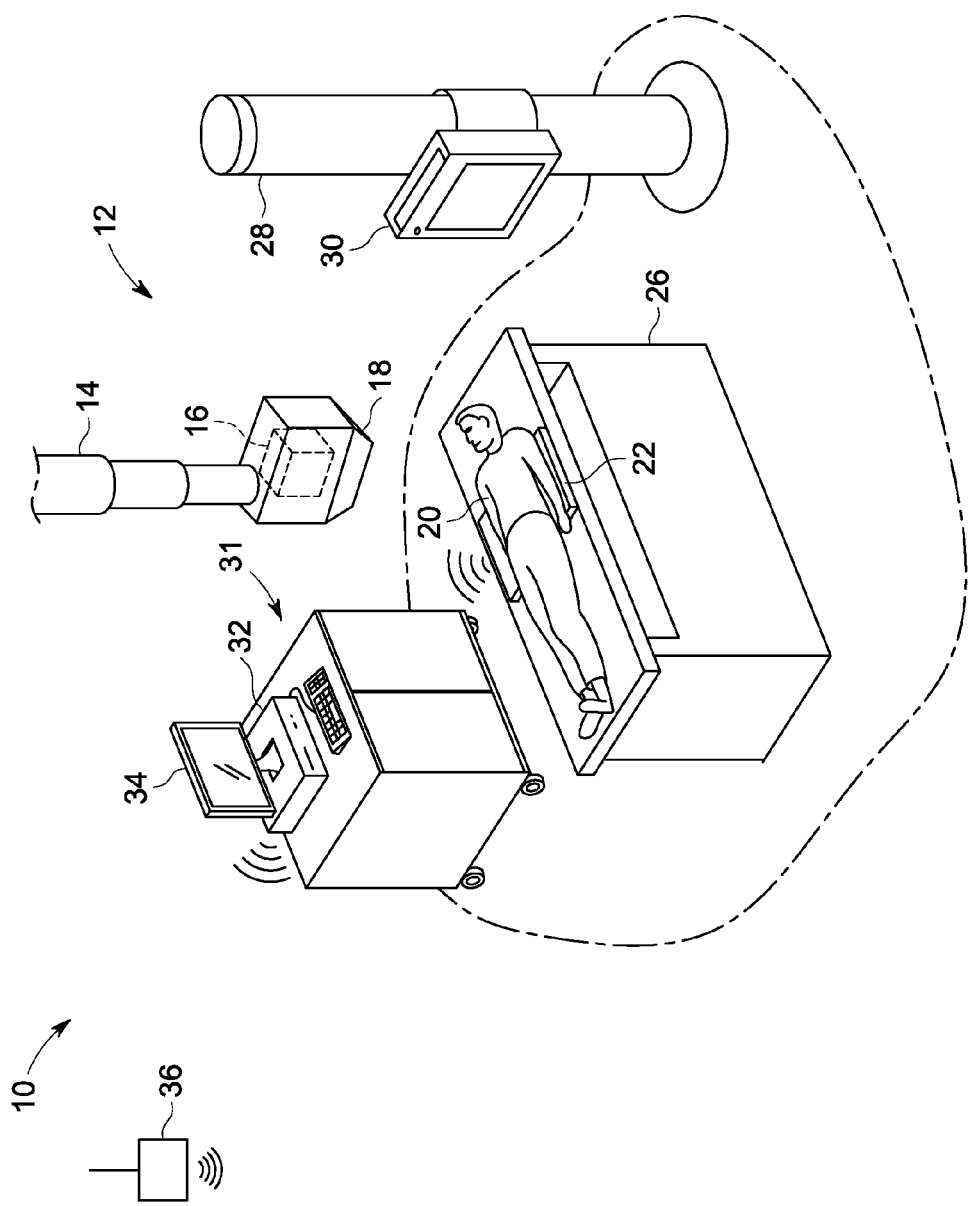
FIG. 1 is perspective view of an embodiment of a fixed X-ray system, equipped in accordance with aspects of the present disclosure.

Referring generally to FIG. 1, an imaging system, in particular an X-ray system is represented and referenced generally by reference numeral 10. In the illustrated embodiment, the X-ray system 10 is a digital X-ray system. The X-ray system 10 is designed both to acquire original image data and to process the image data for display in accordance with present techniques. In the embodiment illustrated in FIG. 1, the X-ray system 10 includes an imager system 12. The imager system 12 includes an overhead tube support arm 14 for positioning a radiation source 16, such as an X-ray tube, and a collimator 18 with respect to a patient 20 and a portable digital X-ray detector 22. In one embodiment, the imager system 12 may be used in consort with one or both of a patient table 26 and a wall stand 28 to facilitate image acquisition. Particularly, the table 26 and the wall stand 28 may be configured to receive the detector 22. For instance, the detector 22 may be placed on an upper, lower, or intermediate surface of the table 26, and the patient 20 (more specifically, an anatomy of interest of the patient 20) may be positioned on the table 26 between the detector 22 and the radiation source 16. The wall stand 28 may include a receiving structure 30 also adapted to receive the detector 22, and the patient 20 may be positioned adjacent the wall stand 28 to enable the image data to be acquired via the detector 22. The receiving structure 30 may be moved vertically along the wall stand 28.

Also depicted in FIG. 1, the imager system 12 includes a systems cabinet 31 that includes a workstation 32 and display 34. In one embodiment, the workstation 32 may include or provide the functionality of the imager system 12 such that a user, by interacting with the workstation 32, may control operation of the source 16 and detector 22. The detector 22 may be in communication with the workstation 32 as described below. The workstation 32 may house systems electronic circuitry that acquires image data from the detector 22 and that, where properly equipped (e.g., when the workstation 32 includes processing circuitry), may process the data to form desired images. In addition, the systems electronic circuitry both provides and controls power to the X-ray source 16. The workstation 32 may include buttons, switches, or the like to facilitate operation of the X-ray source 16 and detector 22. In one embodiment, the workstation 32 may be configured to function as a server of instructions and/or content on a network 36 of the medical facility, such as a hospital information system (HIS), a radiology information system (RIS), and/or picture archiving communication system (PACS). In certain embodiments, the workstation 32 and/or detector 22 may wirelessly communicate with the network 36.

In present embodiments, the detector 22 includes circuitry for processing the image data received through the detector 22 before communicating the image data to the workstation 32. The detector 22 may convert analog signals from detector elements to digital pixel values. The detector 22 may include an index value source for generating digital index values with a smaller bit-width than the digital pixel values. This reduces the digital representation of the image data collected by the detector 22, thereby reducing the data transfer time between the detector 22 and the workstation 32.

In one embodiment, the imager system 12 may be a stationary system disposed in a fixed X-ray imaging room, such as that generally depicted in and described above with respect to FIG. 1. It will be appreciated, however, that the presently disclosed techniques may also be employed with other imaging systems, including mobile X-ray units and systems, in other embodiments.

Figure 2:
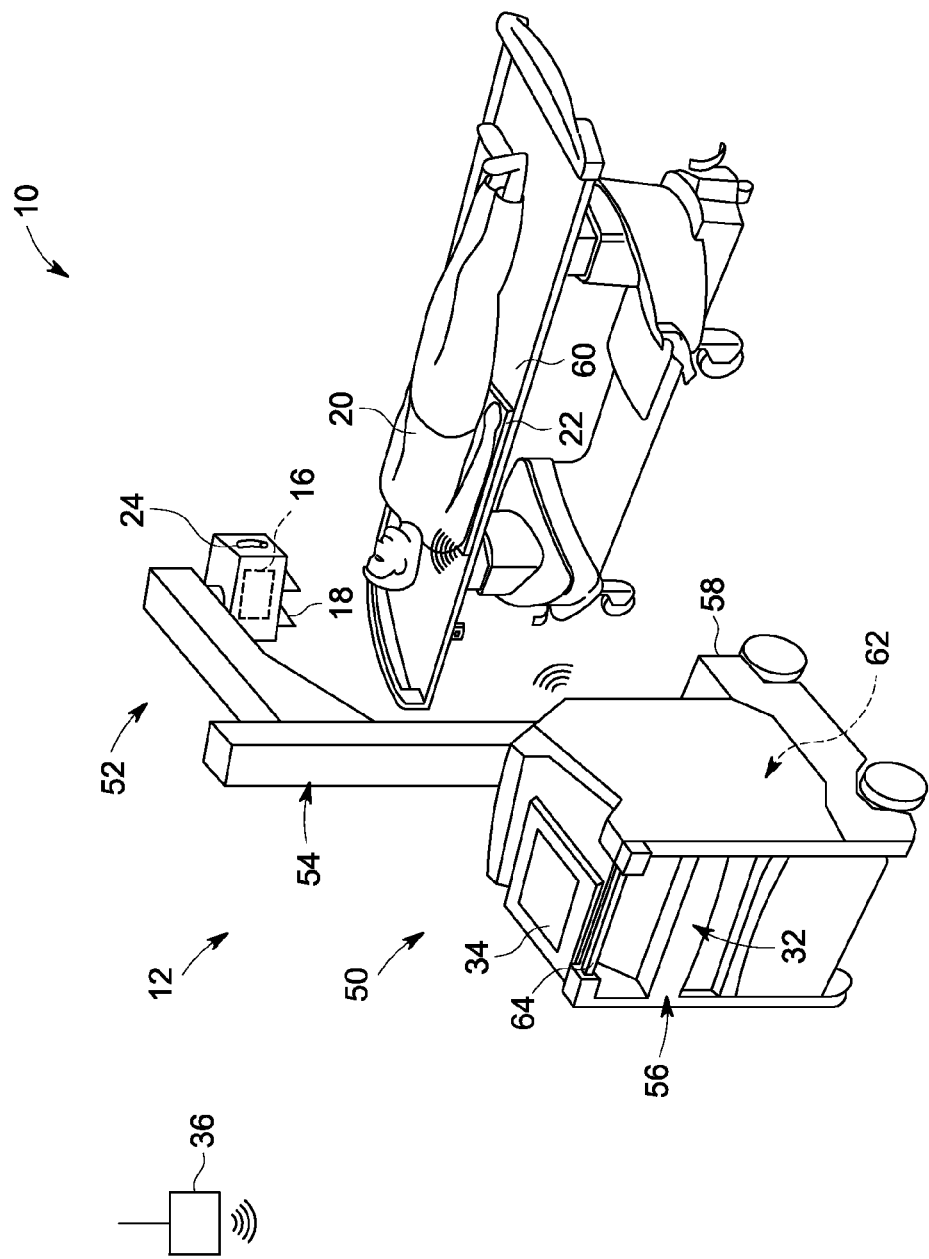
FIG. 2 is a perspective view of an embodiment of a mobile X-ray system.

For instance, as illustrated in the medical imaging system 10 (e.g., X-ray system) of FIG. 2, the imager system 12 may be moved to a patient recovery room, an emergency room, a surgical room, or any other space to enable imaging of the patient 20 without requiring transport of the patient 20 to a dedicated (i.e., fixed) X-ray imaging room. The X-ray system 10 includes a mobile imager or mobile X-ray base station 50 and a portable digital X-ray detector 22. As above, the illustrated X-ray system 10 is a digital X-ray system. In one embodiment, a support arm 52 may be vertically moved along a support column 54 to facilitate positioning of the radiation source 16 and collimator 18 with respect to the patient 20. Further, one or both of the support arm 52 and support column 54 may also be configured to allow rotation of the radiation source 16 about an axis. In addition, the X-ray base station 50 has a wheeled base 58 for movement of the station 50.

The patient 20 may be located on a bed 60 (or gurney, table or any other support) between the X-ray source 24 and the detector 22 and subjected to X-rays that pass through the patient 20. During an imaging sequence using the digital X-ray system 10, the detector 22 receives X-rays that pass through the patient 20 and transmits imaging data to a base unit 56. The detector 22 is in wireless communication with the base unit 56. The base unit 56 houses systems electronic circuitry 62 that acquires image data from the detector 22 and that, where properly equipped, may process the data to form desired images. In addition, the systems electronic circuitry 62 both provides and controls power to the X-ray source 16 and the wheeled base 58. The base unit 56 also has the operator workstation 32 and display 34 that enables the user to operate the X-ray system 10. The operator workstation 32 may include buttons, switches, or the like to facilitate operation of the X-ray source 16 and detector 22. In one embodiment, the workstation 32 may be configured to function as a server of instructions and/or content on the network 36 of the medical facility, such as HIS, RIS, and/or PACS. In certain embodiments, the workstation 32 and/or detector 22 may wirelessly communicate with the network 36.

Similar to the X-ray system 10 in FIG. 1, components of the imager system 12 (e.g., base unit 56) and the detector 22 are configured to reduce a size of the digital representation of the image communicated between the detector 22 and the base unit 56. These components may decrease the digital representation size of an image collected by the detector 22 and transmit the compressed digital image over a communication channel. When the compressed image reaches the base unit 56, the electronic circuitry 62 may increase the digital representation to a desired bit-width for the display 34.

Figure 3:
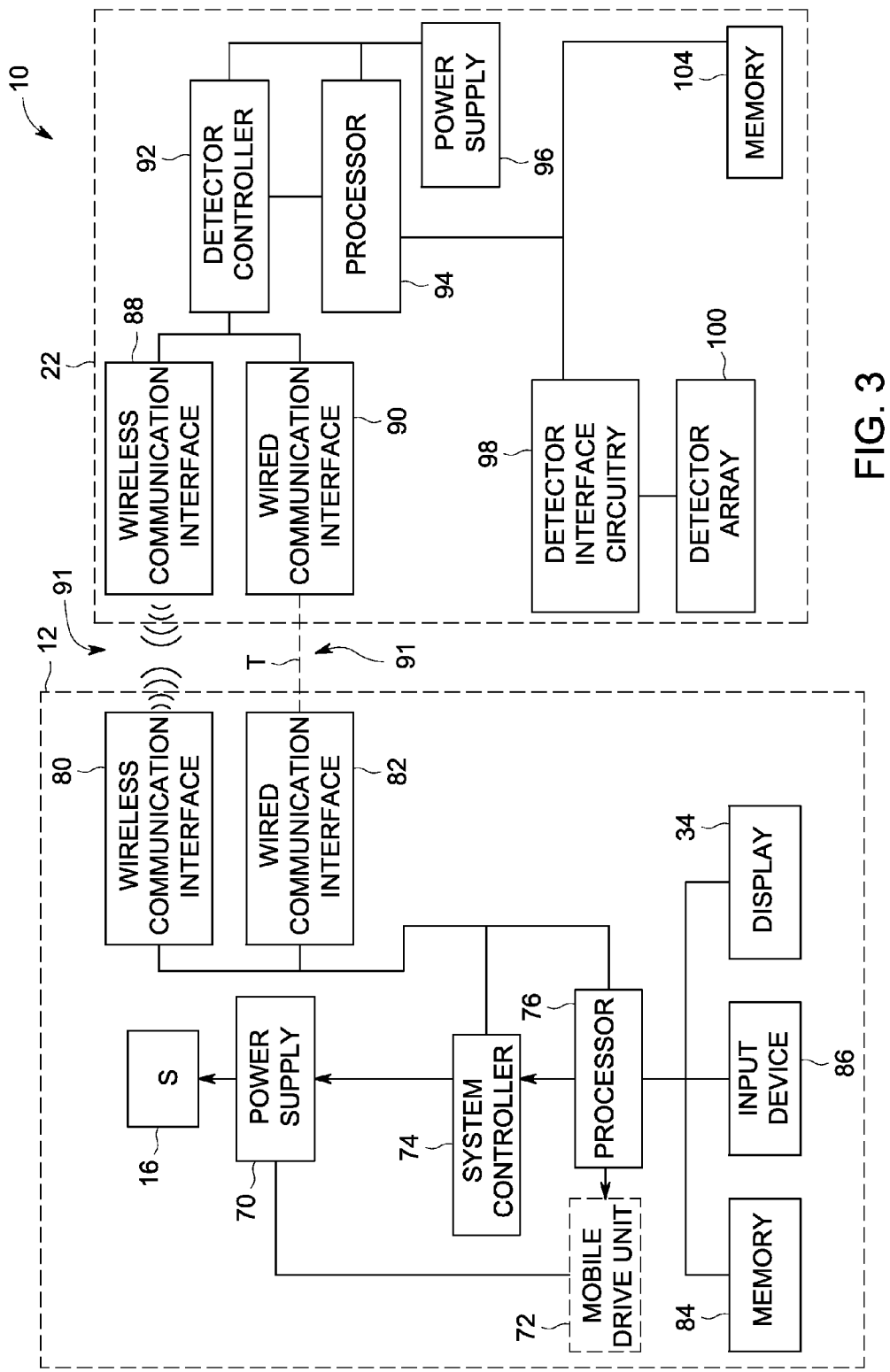
FIG. 3 is a diagrammatical overview of an embodiment of an X-ray system.

Regardless of the differences between the X-ray systems 10 shown in FIGS. 1 and 2, certain features internal to the X-ray system 10 remain consistent across different embodiments. These components are illustrated diagrammatically in FIG. 3. The imager system 12 includes the X-ray source 16 of radiation. The X-ray source 16 is controlled by a power supply 70, which furnishes both power and control signals for examination sequences. In addition, in mobile imaging systems the power supply 70 furnishes power to a mobile drive unit 72 of the wheeled base 58. The power supply 70 is responsive to signals from a system controller 74. In general, the system controller 74 commands operation of the imaging system to execute examination protocols and to process acquired image data. In the present context, the system controller 74 also includes signal processing circuitry, typically based upon a general purpose or application-specific digital computer, associated memory circuitry for storing programs and routines executed by the computer, as well as configuration parameters and image data, interface circuits, and so forth. The system controller 74 may include or may be responsive to a processor 76. The processor 76 receives image data from the detector 22 and processes the data to reconstruct an image of a subject.

The processor 76 is linked to a wireless communication interface 80 that allows wireless communication with the detector 22. Further, the processor 76 is linked to a wired communication interface 82 that allows communication with the detector 22 via a tether (e.g., a multi-conductor cable). The imager system 12 may also be in communication with a server. The processor 76 is also linked to a memory 84, an input device 86, and the display 34. The memory 84 stores configuration parameters, calibration files received from the detector 22, and lookup tables used for image data processing. The input device 86 may include a mouse, keyboard, or any other device for receiving user input, as well as to acquire images using the imager system 12. The display 34 allows visualization of output system parameters, images, and so forth.

The detector 22 includes a wireless communication interface 88 for wireless communication with the imager system 12, as well as a wired communication interface 90, for communicating with the detector 22 when it is tethered to the imager system 12. The detector 22 may also be in communication with a server. The wireless communication interfaces 80 and 88, as well as the wired communication interfaces 82 and 90, define a communication channel 91 between the imager system 12 and the detector 22, over which digital X-ray images are transmitted. It is noted that the wireless communication interface 88 may utilize any suitable wireless communication protocol, such as an ultra wideband (UWB) communication standard, a Bluetooth communication standard, or any 802.11 communication standard. Moreover, the detector 22 is coupled to a detector controller 92 which coordinates the control of the various detector functions. For example, the detector controller 92 may execute various signal processing and filtration functions, such as for initial adjustment of dynamic ranges, interleaving of digital image data, and so forth. The detector controller 92 is responsive to signals from the system controller 74, as well as the detection circuitry 78. The detector controller 92 is linked to a processor 94. The processor 94, the detector controller 92, and all of the circuitry receive power from a power supply 96. The power supply 96 may include a battery. Alternatively, the detector 22, including the power supply 96, may receive power from the power supply 70 when tethered to the imager system 12.

Also, the processor 94 is linked to detector interface circuitry 98. The detector 22 converts X-ray photons received on its surface to lower energy photons. The detector 22 includes a detector array 100 that includes an array of photodetectors to convert the light photons to electrical signals. Alternatively, the detector 22 may convert the X-ray photons directly to electrical signals. These electrical signals are converted to digital values by the detector interface circuitry 98 which provides the values to the processor 94 to be converted to imaging data and sent to the imager system 12 to reconstruct an image of the features within a subject. Alternatively, the imaging data may be sent from the detector 22 to a server to process the imaging data.

Further, the processor is linked to a memory 104. The memory 104 may store various configuration parameters, calibration files, and detector identification data. In addition, the memory 104 may store one or more lookup tables used by the processor 94 to quantize image data before communicating the data over the communication channel 91. In certain embodiments, the lookup tables stored in the memory 104 of the detector 22 may also be stored in the memory 84 of the imager system 12, in order to process the compressed image data received from the detector 22.

In order to reduce image transfer time across the communication channel 91, present embodiments of the detector 22 include image processing components (e.g., processor 94) for reducing a size of the image for transmission across the communication channel 91. This is accomplished without reducing the number of pixels of the image, as this would compromise the resolution of the X-ray imaging system 10. Instead, the image processing components are configured to alter the digital representation of the pixels themselves. That is, the image processing components reduce the representation of each pixel from a 14-bit binary word to smaller bit-width.

Such compression of the digital pixel representation may lead to an increase in quantization noise in the X-ray image data. This quantization noise contributes to the total noise within the X-ray image data according to the following equation:

$$\sigma_T = \sqrt{\sigma_Q^2 + \sigma_E^2 + o\delta^2}. \quad (1)$$

In the equation above, $\sigma_T$ represents total noise, $\sigma_Q$ represents X-ray quantum noise, $\sigma_E$ represents electronic noise, and o represents analog-to-digital (A/D) quantization noise. The electronic noise is an inherent level of noise relating to the electronic components operating in the detector 22 and the imager system 12. The electronic noise level does not change throughout use of the X-ray system 10, and the electronics are generally designed in a way to minimize this electronic noise. The X-ray quantum noise is due to the quantum nature of the X-rays, and is proportional to the square root of the number of X-ray photons arriving at the detector 22. Consequently, the X-ray quantum noise is higher when more photons hit the detector 22. Since the number of photons arriving at each detector element may vary, the amount of X-ray quantum noise for each pixel of the X-ray image may vary proportionally.

The A/D quantization noise is related to the step size used in quantizing each pixel into a digital representation. An increase in the step size of a digital quantizer reduces the digital representation of the pixels to a lower bit-width, but it also increases the quantization noise. In order to reduce the digital representation of pixels without increasing the total noise level beyond an acceptable limit, the step size of the quantizer may be chosen such that the A/D quantization noise is maintained below the X-ray quantum noise for each pixel. Thus, the quantizer uses a smaller step size when the X-ray dose is low and a larger step size when the X-ray dose is high. In this way, the total noise is dominated by the quantum noise and is basically independent of the quantization noise. To determine the appropriate step size for quantizing each pixel, the detector 22 may include certain image processing components (e.g., implemented by the processor 94) that make up the quantizer. Throughout the following discussion, the term "quantizer" may be used interchangeably with the term "index value source".

Figure 4:
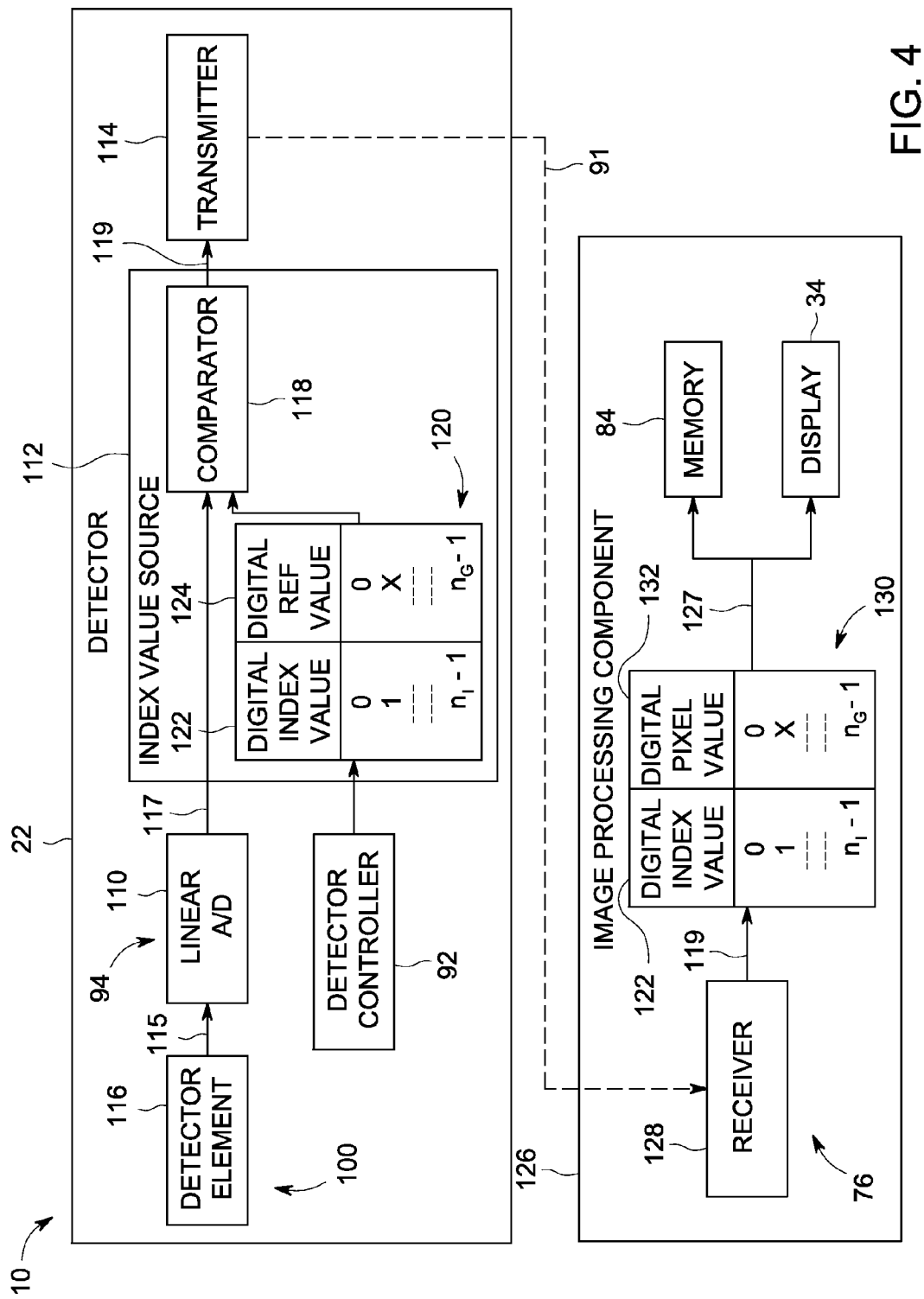
FIG. 4 is a diagrammatical representation of an embodiment of certain components of the X-ray system of FIG. 3.

These image processing components are illustrated in detail in FIG. 4. The detector 22 includes, for example, an analog-to-digital (A/D) converter 110, an index value source 112 (or quantizer), and a transmitter 114. The A/D converter 110 is configured to receive an analog pixel value 115 from a detector element 116 of the detector array 100, and convert the analog pixel value 115 into a digital pixel value 117. In the illustrated embodiment, the A/D converter 110 is a linear A/D converter configured to convert the analog pixel value 115 into a 14-bit digital pixel value. The index value source 112 receives the digital pixel value 117 from the linear A/D converter 110 and generates a digital index value 119 based on a comparison of the digital pixel value 117 to a digital reference value, as discussed in detail below. This digital index value 119 may have a smaller bit-width than the digital pixel value 117 received by the index value source 112. In this way, the index value source 112 acts as a quantizer to compress the X-ray image for communication over the communication channel 91.

In the illustrated embodiment, the index value source 112 includes a comparator 118 and a lookup table 120 used to determine the digital index value 119 appropriate for the digital pixel value 117 received from the A/D converter 110. The lookup table includes a mapping of digital index values 122 to digital reference values 124, and the comparator is designed to compare the incoming digital pixel value 117 with the digital reference values 124. As illustrated, the digital index values 122 may include integers that go from 0 to 1 to 2, all the way through $n_I-1$, where $n_I$ is a total number of values that can be represented with $\log 2(n_I)$ binary bits. Similarly, the digital reference values 124 may include integers that go from 0 to $n_G-1$, where $n_G$ is a total number of gray levels that can be represented with $\log 2(n_G)$ binary bits. In certain X-ray systems 10, the total number $n_G$ of gray levels is 16384, which can be expressed in 14 bits. In present embodiments, $n_G$ is greater than $n_I$. This ensures that the digital index value 119 output from the index value source 112 has a smaller bit-width than the input digital pixel value 117. Consequently, the size of the image representation transferred over the communication channel 91 is significantly reduced.

In certain embodiments, the mapping of digital index values 122 to digital reference values 124 is at least partially non-linear. The mapping is representative of the relationship between the increasing quantum noise $\sigma_Q$ and the increasing quantization noise $\sigma_\delta$. Again, as the number of photons hitting the detector element 116 increases, the quantum noise $\sigma_Q$ increases. This increase in the quantum noise $\sigma_Q$ enables an increase in the quantization noise o according to the formula described above, and this amount of allowable quantization noise corresponds with a given number $n_I$ of steps. The lookup table 120 representing the relationship between $n_G$ and $n_I$ may be determined by the detector controller 92 in order to reduce the total noise $\sigma_T$ in the system while allowing the fewest number $n_I$ of steps (or digital index values 122).

The comparator 118 is used to determine the digital index value 119 that corresponds with the digital pixel value 117 received from the A/D converter 110. Specifically, the comparator 118 receives the digital pixel value 117, and one of the digital reference values 124 at a time. As the digital index value 122 tracks up from 0 to $n_I$1, the corresponding digital reference value 124 goes up gradually, according to the relationship maintained in the lookup table 120. When the digital reference value 124 reaches the same level as the digital pixel value 117 in the comparator 118, the comparator 118 locks its output with the digital index value 122 corresponding to the current digital reference value 124. Thus, the comparator 118 performs the quantization of the digital pixel value 117 of each detector element 116. In certain embodiments, the comparator 118 includes two or more stages for performing this quantization, as described in detail below.

The comparator 118, which is a digital comparator, may be implemented with the processor 94, a digital computer, a microcontroller, or the like.

The quantization process described above may be performed for each detector element 116 within the detector array 100 before the determined digital index values 119 for the entire image are transmitted over the communication channel 91. In other embodiments, the detector 22 may send the digital index values 119 corresponding to each of the detector elements 116 as each one becomes available. In either case, the digital index values 119 are transferred from the detector 22 to an image processing component 126 used to process the image data collected by the detector 22. As illustrated, the detector 22 may communicate the digital index values 119 to an entirely separate image processing component 126. In such instances, the image processing component 126 may be resident in the imager system 12 and representative of certain components implemented through the processor 76.

The transmitter 114 of the detector 22 may send the determined digital index values 119 from the index value source 112 to a receiver 128 of the image processing component 126 over the communication channel 91. The communication channel 91 may be a tether or a wireless link, as described with reference to FIG. 3. In embodiments having a tether for such communication, the transmitter 114 functions as the wired communication interface 90 and the receiver 128 functions as the wired communication interface 82. Similarly, in wireless embodiments, the transmitter 114 functions as the wireless communication interface 88 (e.g., wireless transmitter), and the receiver 128 functions as the wireless communication interface 80.

Upon receiving the digital index value 119 from the transmitter 114, the image processing component 126 is designed to generate another digital pixel value 127 based at least in part on the received digital index value 119 and a lookup table 130 of the image processing component 126. This lookup table 130 includes a mapping between the digital index values 122 and digital pixel values 132 for the final X-ray image. In the illustrated embodiment, the lookup table 130 is the same as the lookup table 120 used in the index value source 112. That is, the index value source 112 generates the digital index value 119 based on the lookup table 120, and the image processing component 126 maps the generated digital index value 119 to the digital pixel value 127 using the same lookup table 120. This may be desirable when the number of gray levels for the final X-ray image is the same as the number of gray levels $n_G$ used in the detector 22. In some embodiments, the lookup table 130 of the image processing component 126 may be adjusted from the lookup table 120 of the index value source 112 to make a mean of the quantization error approximately equal to zero. This adjustment may account for an amount of offset in the mapping of digital index values to digital reference values. In such embodiments, the detector controller 92 may provide the lookup table 120 to the processor 76 via the communication channel 91 and detection circuitry 78. By reducing the bit-width of the image representation sent over the communication channel 91 and increasing the bit-width once the image is received by the image processing component 126, the imaging system 10 allows for reduced image transfer time without an undesirable loss in image quality.

By using the lookup table 130, the image processing component 126 may generate the digital pixel value 127 having a bit-width larger than the bit-width of the received digital index value 119. Again, this provides a decreased amount of data transferred over the communication channel 91 without an undesirable decrease in image quality. The generated digital pixel value 127 may be stored in a memory (e.g., 84) of the image processing component 126. In addition, the generated digital pixel value 127 may be provided to a display (e.g., 34) of the image processing component 126, allowing a user to view the image relatively quickly after image detection takes place.

Figure 5:
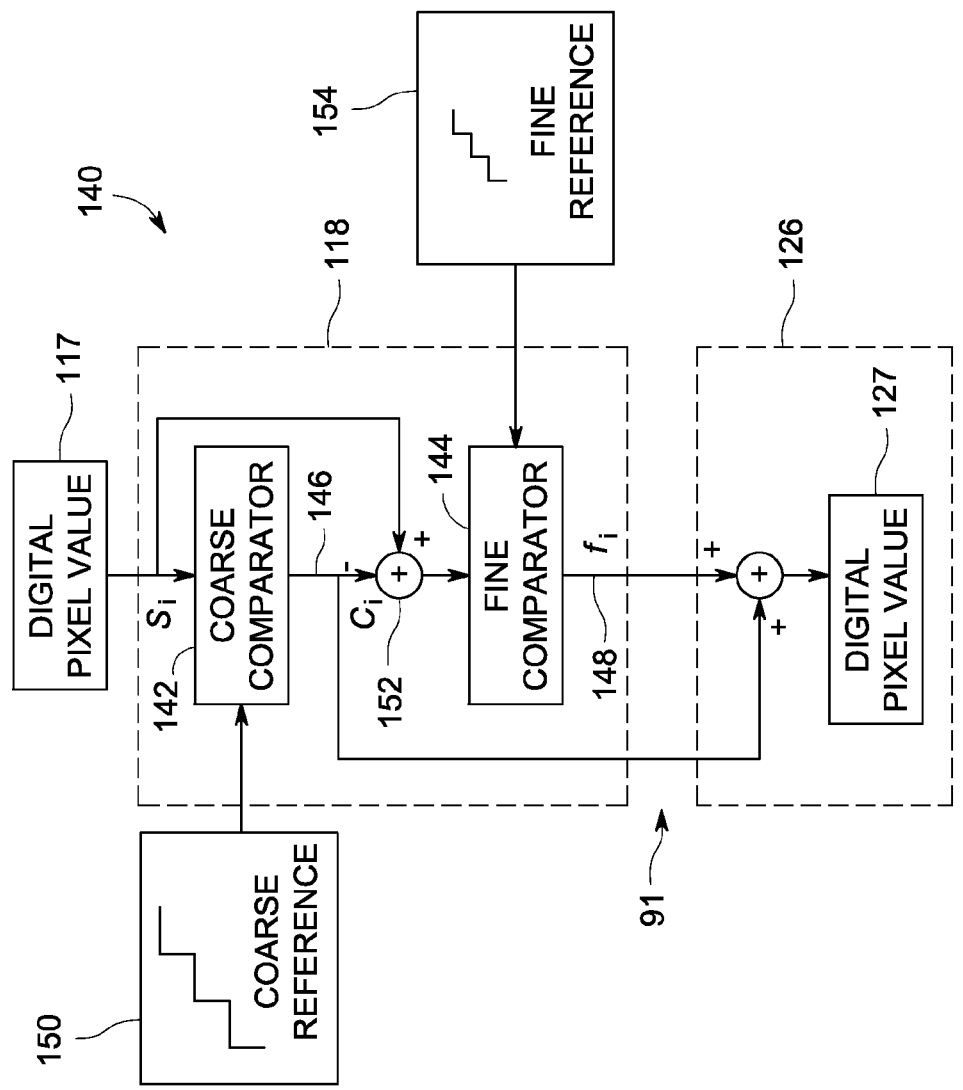
FIG. 5 is a diagrammatical representation of an embodiment of a two-stage comparator for use in the X-ray system of FIG. 4.

As mentioned above, the comparator 118 may include multiple stages, such as two or more digital comparators in series. FIG. 5 is a diagrammatical representation of a two-stage comparator 140 for use in the X-ray system 10. The illustrated two-stage comparator 140 includes a coarse comparator 142 and a fine comparator 144. The coarse comparator 142 is used to generate a coarse digital index value 146, and the fine comparator 144 is used to generate a fine digital index value 148. The coarse and fine digital index values 146 and 148 may both be transferred from the detector 22 to the image processing component 126, and the image processing component 126 may be configured to generate the digital pixel value 127 based on the coarse and fine digital index values 146 and 148.

The following description is one example of the use of coarse and fine comparators 142 and 144 to compress an image for transmission. The digital pixel value 117, which is generally denoted in the illustrated embodiment as $s_i$, is received by the coarse comparator 142. The coarse comparator 142 then compares the digital pixel value 117 with coarse digital reference values 150. The coarse digital reference values 150 may be maintained in a lookup table with associated coarse digital index values, similar to the lookup table 120 of FIG. 4. The coarse comparator 142 steps through the coarse digital reference values 150, comparing these to the digital pixel value 117 until the coarse digital reference value 150 reaches or exceeds the digital pixel value 117. When this occurs, the coarse comparator 142 locks in the coarse digital index value 146 (denoted as $c_i$) associated with the coarse digital reference value 150.

After determining the coarse digital index value 146, the comparator 118 calculates (152) a weighted difference between the coarse digital index value 146 and the digital pixel value 117. That is, the coarse digital index value 146 may be multiplied by a constant and subtracted from the digital pixel value 117, and the calculated difference is input to the fine comparator 144. The fine comparator 144 is configured to compare the calculated difference with fine digital reference values 154 in order to determine the fine digital index value 148 (denoted as $f_i$). The digital index value 119 sent to the image processing component 126 includes both the coarse digital index value 146 received from the coarse comparator 142 and the fine digital index value 148 received from the fine digital comparator 144.

In one embodiment, the digital pixel value 117 input to the two-stage comparator 140 includes a value that can be expressed in 14 bits (e.g., 1 to 16384), while the output digital index value 119 can be expressed in 8 bits. To accomplish this, the two-stage comparator 140 may determine two 7-bit index values $c_i$ and $f_i$ to represent the 14-bit digital pixel value 117. The coarse and fine comparators 142 and 144 may be linear, the coarse comparator 142 having a step size of 128 and the fine comparator 144 having a step size of 1. The weighted difference input to the fine comparator 144 may be calculated, as indicated by reference numeral 152 by the following expression: $s_i - c_i \times 2^7$.

Since the digital index values 146 and 148 each range from 0 to 128, the digital representation sent across the communication channel 91 may be 8-bits (7-bits plus 7-bits), instead of the original 14-bits. In other words, the combined bit-width of the coarse and fine digital index values 146 and 148 is smaller than the bit-width of the first digital pixel value 117. The image processing component 126 may generate the digital pixel value 127 represented by the 8-bit transmission according to the following expression: $c_i \times 2^7 + f_i$.

It should be noted that other types of multi-stage comparators 140 may be used in the index value source 112 of the detector 22 in the X-ray system 10. The multi-stage comparator 140 may compress the incoming digital pixel value 117 into digital index values with other desired bit-widths, instead of 7-bits each. In addition, other embodiments of the multi-stage comparator 140 may include non-linear mappings between the coarse and fine digital reference values 150 and 154 and their respective index values. Many other types and configurations of digital comparators 118 may be utilized within the detector 22 to reduce a size of the image representation and, consequently, image transfer time over the communication channel 91.

Figure 6:
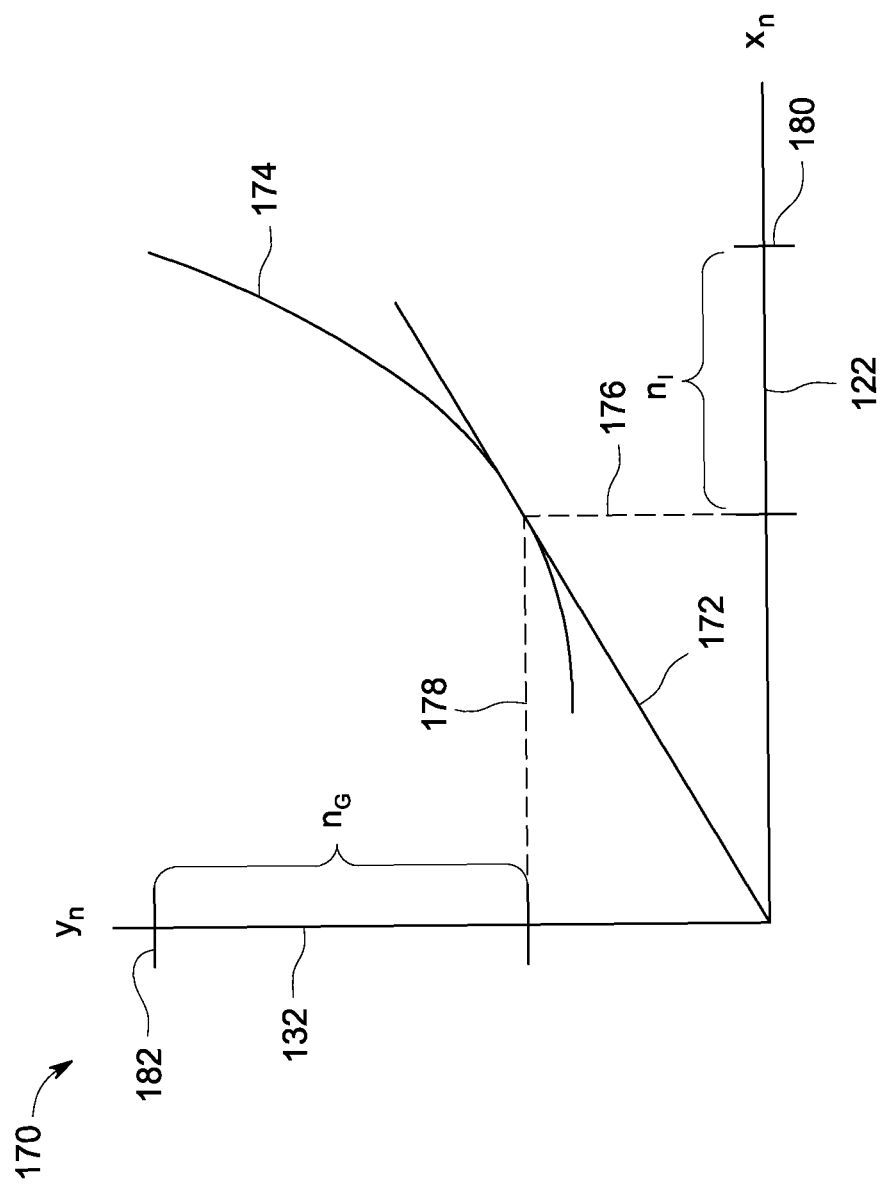
FIG. 6 is a plot illustrating an embodiment of linear-quadratic mapping between digital index values and digital pixel values.

The mapping between digital index values 122 and digital reference values 124 maintained in the lookup table 120 of the index value source 112 and/or the image processing component 126 may be non-linear. That is, unlike the digital reference values 150 and 154 described in FIG. 5, the digital reference values 124 may have varying step sizes. FIG. 6 illustrates a plot 170 modeling a linear-quadratic mapping between the digital index values 122 and the digital pixel values 132, which may be maintained in the lookup table 130. This linear-quadratic mapping may be used to generate the digital pixel value 127 from the digital index value 119 received by the image processing component 126. The plot 170 illustrates digital pixel values 132 (ordinate) against digital index values 122 (abscissa), and the plot 170 includes a linear section 172 and a quadratic section 174. The linear section 172 extends from zero to linear index value limits 176 and 178. This type of mapping may be especially useful when the digital pixel value 127 contains an offset. This offset could represent any number of offsets to the first digital pixel value 117 across a range of temperatures, frame rates, and part to part variations within the system components, among other things. For example, when the X-ray system 10 is operating under certain temperature conditions, the dynamic range of the digital pixel values 117 received from the detector element array 100 may be different or offset from the desired dynamic range for the digital pixel values 127 to be stored/displayed. The quadratic section 174 represents the relationship between the digital pixel values 132 and the digital index values 122 outside of this offset. As the digital index values 122 increase, the step size between subsequent corresponding digital pixel values 132 increase as well. This quadratic section 174 extends from the linear index value limits 176 and 178 to quadratic index value limits 180 and 182, respectively. In certain embodiments, the quadratic section 174 extends across $n_I$ values along the axis of digital index values 122, and across $n_G$ values along the axis of digital pixel values 132. The illustrated linear-quadratic mapping may be modeled with the following two-part equation:

$$y_n = b \cdot x_n \text{ when } x_n \leq n_L \text{ and} \qquad (2)$$

$$y_n = b \cdot n_L + c \cdot (x_n - n_L)^2 \text{ when } x_n > n_L. \qquad (3)$$

In the above equation, b and c are constant coefficients determined based on the configuration of the particular X-ray system 10. $x_n$ is the input, which may represent the digital index value 119 generated by the index value source 112 and communicated to the image processing component 126. $y_n$ is the output, which may represent the digital pixel value 127 generated based on the received digital index value 119. $n_L$, is the number of linear levels within the model, based on the amount of pixel value offset in the digital index values 122. This equation may be utilized to map the digital index values 122 with their corresponding digital pixel values 132 and/or digital reference values 124. Again, this mapping may be determined by the detector controller 92 based on the relationship between X-ray quantum noise $\sigma_Q$, which increases with respect to the detected analog pixel value 115, and quantization noise $\sigma_\delta$.

Figure 7:
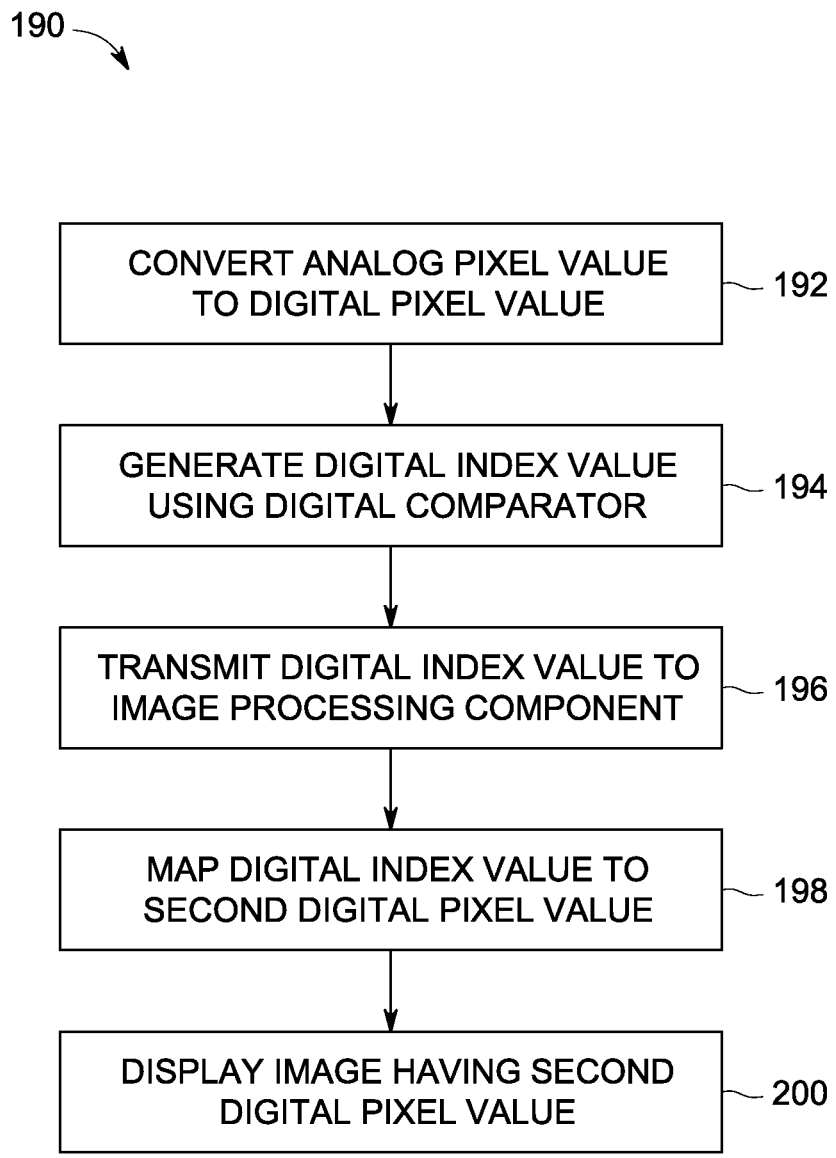
FIG. 7 is a process flow diagram of an embodiment of a method for operating an X-ray system.

FIG. 7 is a process flow diagram of a method 190 for operating the X-ray system 10. The method 190 includes converting (block 192) the analog pixel value 115 to the digital pixel value 117 using the linear A/D converter 110. The method 190 also includes generating (block 194) the digital index value 119 based on a comparison of the digital pixel value 117 to one or more of the digital reference values 122 using the digital comparator 118. This may be accomplished through the use of the lookup table 120 mapping the digital index values 122 to the digital reference values 124. In some embodiments, generating the digital index value 119 includes generating the coarse digital index value 146 and the fine digital index value 148, as discussed in reference to FIG. 5. In certain embodiments, the method 190 includes transmitting (block 196) the digital index value 119 from the index value source 112 having the comparator 118 to the image processing component 126 via the transmitter 114. Further, the method 190 includes mapping (block 198) the generated digital index value 119 to the digital pixel value 127 via the image processing component 126, where the digital pixel value 127 has a larger bit-width than the digital index value 119. This may be accomplished by using an equation that is at least partially quadratic, such as the equation described in reference to FIG. 6. The mapping (block 198) may be based on the same lookup table 120 used to map digital index values 122 to digital reference values 124 in the index value source 112. The method 190 also may include displaying (block 200) an image on the display 34 of the image processing component 126, where the image includes the digital pixel value 127 generated by the image processing component 126.

Technical effects of the disclosed embodiments include the ability to, among other things, decrease image transfer time across the communication channel between the X-ray detector and the imager system. The use of a quadratic mapping between pixel values and index values may allow for substantially more compression of the image than would be possible with a linear mapping, due to the relationship between quantum noise and quantization noise. That is, the higher the X-ray intensity for a given pixel, the higher the step size selected for quantizing the pixel value to an index value. The use of a multi-stage comparator may allow smaller representations of the digital pixel values for communication through two or more relatively simple, linear mappings of pixel values to coarse and fine index values that can be communicated to the image processing component. The linear A/D converter may convert the analog signal to a full-sized digital representation before the digital value is quantized, saving processing time within the system.

This written description uses examples to disclose the present subject matter, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A digital X-ray detector for use in an imaging system, the digital X-ray detector comprising:
a linear analog-to-digital converter configured to convert an analog pixel value received from a detector element to a digital pixel value; and
an index value source configured to receive the digital pixel value and to generate a digital index value corresponding to the received digital pixel value, the digital index value having a smaller bit-width than the digital pixel value, wherein the index value source comprises a coarse digital comparator configured to generate a coarse digital index value and a fine digital comparator configured to generate a fine digital index value, and wherein the coarse digital comparator is configured to compare a coarse digital reference value with the digital pixel value to determine the coarse digital index value, and the fine digital comparator is configured to compare a fine digital reference value to a calculated weighted difference between the coarse digital index value and the digital pixel value to determine the fine digital index value;
wherein the digital X-ray detector is configured to communicate the digital index value to a separate image processing component.

2. The digital X-ray detector of claim 1, comprising a wireless transmitter for wirelessly transmitting the digital pixel value from the digital X-ray detector to the separate image processing component.

3. The digital X-ray detector of claim 1, wherein the coarse and fine digital index values have a smaller combined bit-width than the digital pixel value.

4. A method of operating a digital X-ray detector, comprising:
converting, via an analog-to-digital converter, an analog pixel value received from a detector element to a digital pixel value;
generating, via an index value source, a digital index value corresponding to the digital pixel value, wherein the digital index value has a smaller bit-width than the digital pixel value, wherein generating the digital index value comprises generating a coarse digital index value and a fine digital index value, and wherein generating the coarse and fine digital index values comprises comparing a coarse digital reference value with the digital pixel value to determine the coarse digital index value using a coarse digital comparator, calculating a weighted difference between the determined coarse digital index value and the digital pixel value, and comparing a fine digital reference value with the calculated difference to determine the fine digital index value using a fine digital comparator; and
communicating the digital index value to a separate image processing component.

5. The method of claim 4, wherein the analog-to-digital converter comprises a linear analog-to digital converter.

6. The method of claim 4, wherein communicating the digital index value to the separate imaging processing component comprises wirelessly transmitting, via a wireless transmitter, the digital pixel value to the separate imaging processing component.

7. The method of claim 4, wherein the index value source comprises a digital comparator, and generating the digital index value corresponding to the digital index value comprises comparing, via the digital comparator, the digital pixel value to a digital reference value.

8. The method of claim 7, wherein the index value source comprises a lookup table relating the digital reference value to the digital index value, and generating the digital index value comprises mapping the digital index value to the digital reference value utilizing the lookup table.

9. A digital X-ray detector for use in an imaging system, the digital X-ray detector comprising:
- a linear analog-to-digital converter configured to convert an analog pixel value into a digital pixel value; and
- an index value source comprising a digital comparator and a lookup table that includes a mapping between the digital index value and a digital reference value, wherein the index value source is configured to receive the digital pixel value from the analog-to-digital converter and to generate, via the digital comparator, a digital index value based on a comparison of the digital pixel value to a digital reference value that utilizes the lookup table, wherein the index value source comprises a coarse digital comparator configured to generate a coarse digital index value and a fine digital comparator configured to generate a fine digital index value, and wherein the coarse digital comparator is configured to compare a coarse digital reference value with the digital pixel value to determine the coarse digital index value, and the fine digital comparator is configured to compare a fine digital reference value to a calculated weighted difference between the coarse digital index value and the digital pixel value to determine the fine digital index value;
- wherein the digital X-ray detector is configured to communicate the digital index value to a separate image processing component.

10. The digital X-ray detector of claim 9, comprising a wireless transmitter for wirelessly transmitting the digital pixel value from the digital X-ray detector to the separate image processing component.

11. The digital X-ray detector of claim 9, wherein the coarse and fine digital index values have a smaller combined bit-width that the digital pixel value.

12. The digital X-ray detector of claim 9, wherein the mapping between the digital index value and the digital reference value is at least partially quadratic.

* * * * *